United States Patent
Zaitsu et al.

(10) Patent No.: US 10,481,128 B2
(45) Date of Patent: Nov. 19, 2019

(54) MASS SPECTROMETER AND BIOLOGICAL SAMPLE ANALYSIS METHOD USING SAID MASS SPECTROMETER

(71) Applicants: SHIMADZU CORPORATION, Kyoto-shi, Kyoto (JP); NATIONAL UNIVERSITY CORPORATION NAGOYA UNIVERSITY, Aichi (JP)

(72) Inventors: Kei Zaitsu, Nagoya (JP); Yumi Hayashi, Nagoya (JP); Tasuku Murata, Kyoto (JP)

(73) Assignees: SHIMADZU CORPORATION, Kyoto-shi, Kyoto (JP); NATIONAL UNIVERSITY CORPORATION NAGOYA UNIVERSITY, Aichi (JP)

( * ) Notice: Subject to any disclaimer, the term of this patent is extended or adjusted under 35 U.S.C. 154(b) by 0 days.

(21) Appl. No.: 16/083,102

(22) PCT Filed: Aug. 26, 2016

(86) PCT No.: PCT/JP2016/075064
§ 371 (c)(1),
(2) Date: Sep. 7, 2018

(87) PCT Pub. No.: WO2017/154240
PCT Pub. Date: Sep. 14, 2017

(65) Prior Publication Data
US 2019/0079050 A1    Mar. 14, 2019

(30) Foreign Application Priority Data
Mar. 9, 2016   (WO) .................. PCT/JP2016/057457

(51) Int. Cl.
*G01N 27/62*   (2006.01)
*G01N 33/50*   (2006.01)
(Continued)

(52) U.S. Cl.
CPC ............ *G01N 27/62* (2013.01); *G01N 33/50* (2013.01); *H01J 49/0031* (2013.01);
(Continued)

(58) Field of Classification Search
CPC . G01N 27/62; G01N 30/7266; H01J 49/0004; H01J 49/161; H01J 49/165
See application file for complete search history.

(56) References Cited

U.S. PATENT DOCUMENTS

| | | | |
|---|---|---|---|
| 2009/0140137 A1* | 6/2009 | Hiraoka | B82Y 35/00 250/282 |
| 2015/0332907 A1* | 11/2015 | Valaskovic | H01J 49/0431 250/282 |

* cited by examiner

*Primary Examiner* — David E Smith
*Assistant Examiner* — Hsien C Tsai
(74) *Attorney, Agent, or Firm* — Sughrue Mion, PLLC

(57) ABSTRACT

In a PESI ion source, a solvent supply unit (8) is placed above the liver (101), which is the object of measurement, and by moving a probe (6) up and down such that the tip of the probe (6) passes through the solvent supply unit (8) and is inserted into the liver (101), a sample is captured by the tip of said probe. The solvent supply unit (8) includes a container unit comprising a liquid-blocking upper film body (81) stretched over the bottom surface opening of a cylindrical body (80), and a liquid-blocking lower film body (82) which is stretched out approximately in parallel with the upper film body (81) with a spacer interposed therebetween; the container unit houses a solvent (84). Because the tip of the probe (6) passes through the solvent (84) during the up-and-down movement of the probe (6), sufficient solvent adheres to the sample and when a high voltage is applied to the probe (6), components in the sample are favorably ionized. Blood seeping from the liver (101) upwards through the hole through which the probe (6) was passed spreads in the periphery of the lower film body (82) and is not admixed into the solvent (84) in the container unit. By this means, it (Continued)

is possible to avoid blood from acting as a contaminant during measurement.

11 Claims, 3 Drawing Sheets

(51) Int. Cl.
*H01J 49/00* (2006.01)
*H01J 49/26* (2006.01)
*H01J 49/04* (2006.01)
*H01J 49/10* (2006.01)

(52) U.S. Cl.
CPC .............. *H01J 49/04* (2013.01); *H01J 49/26* (2013.01); *H01J 49/10* (2013.01)

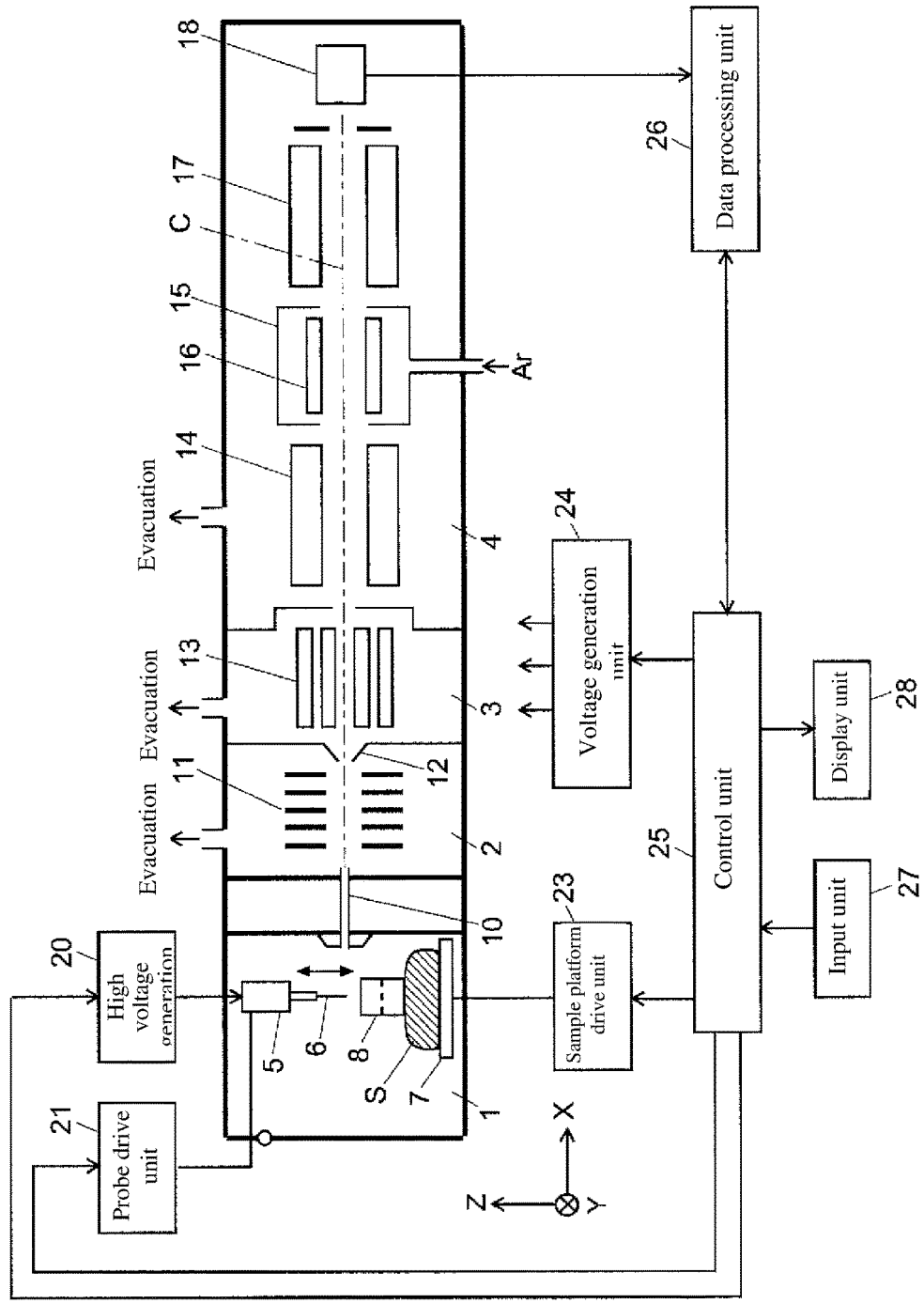
[FIG. 1]

[FIG. 2]
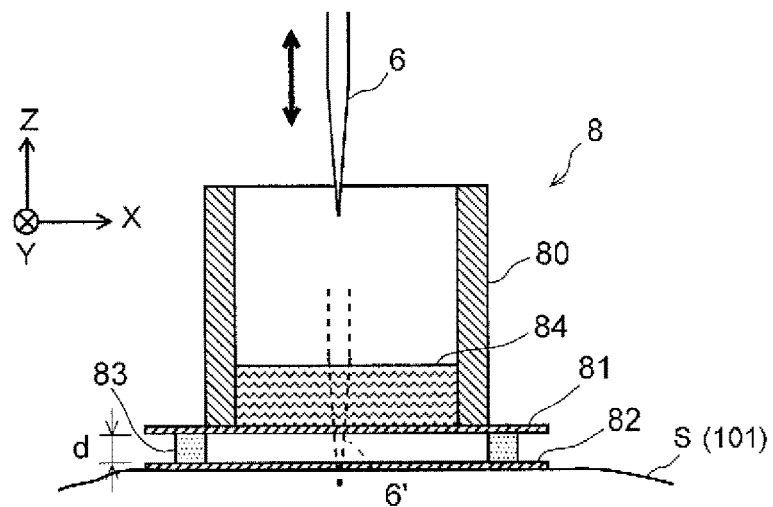
[FIG. 3]
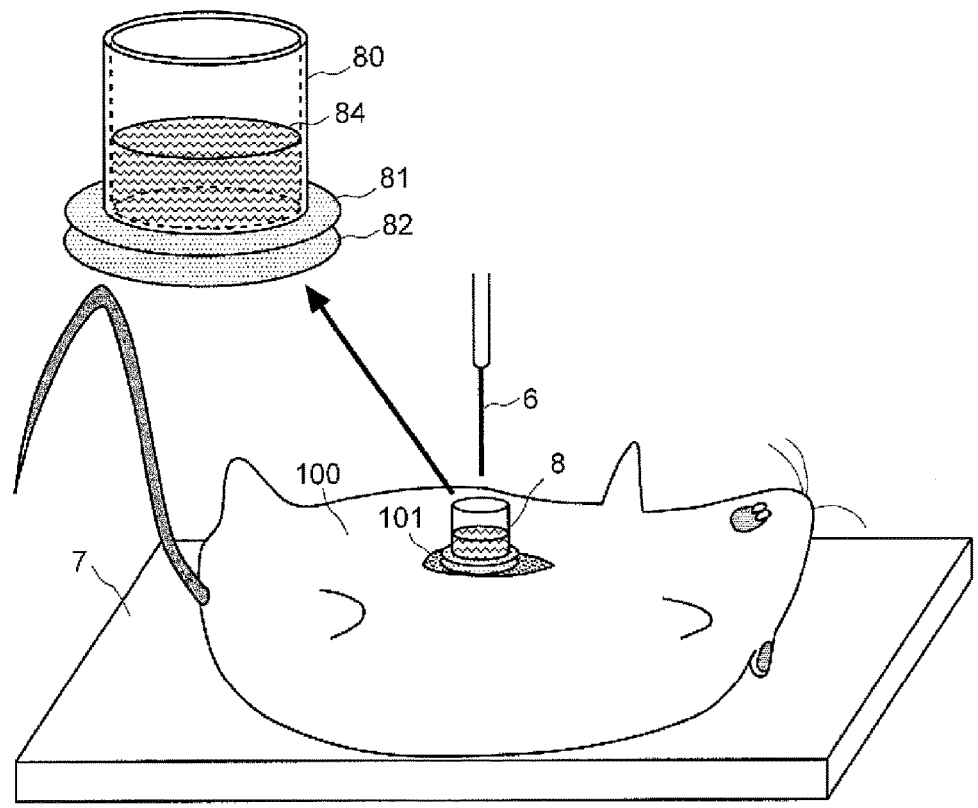

[FIG. 4]
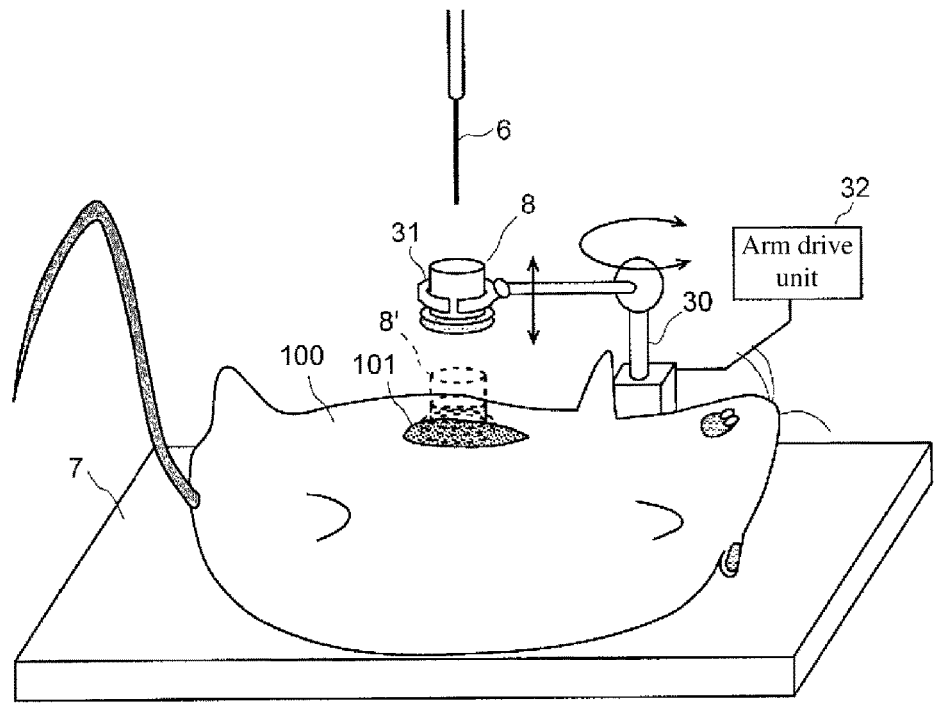
[FIG. 5]
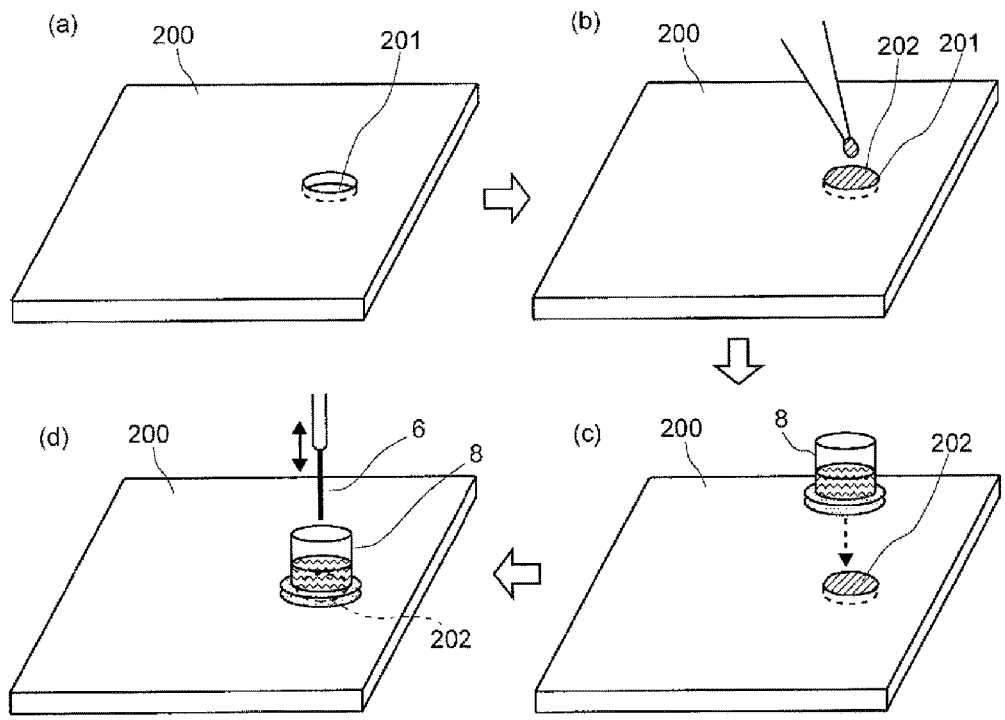

//PAGE START
MASS SPECTROMETER AND BIOLOGICAL SAMPLE ANALYSIS METHOD USING SAID MASS SPECTROMETER

CROSS REFERENCE TO RELATED APPLICATIONS

This application is a National Stage of International Application No. PCT/JP2016/075064 filed Aug. 26, 2016, claiming priority based on International Application No. PCT/JP2016/057457 filed Mar. 9, 2016.

TECHNICAL FIELD

The present invention relates to a mass analysis device and analysis method for biological samples using said device. More specifically, the present invention relates to a mass analysis device comprising an ion source based on a probe electrospray ionization method, and an analysis method suitable for analyzing biological samples in a living state using such a device.

BACKGROUND ART

As ionization methods for ionizing components in a sample which is the object of measurement in a mass analysis device, various methods have been proposed and put to practical use in the prior art. As an ionization method in which ionization is performed in an ambient pressure atmosphere, the electrospray ionization (ESI) method is well known, and one type of ionization method using this ESI that has gained attention in recent years is the probe electrospray ionization (PESI) method.

As disclosed in patent document 1, non-patent document 1, etc., the PESI ion source for performing ionization by the PESI method comprises a conductive probe with a probe diameter of about several hundred nanometers; a displacement unit which moves at least one of either the probe or the sample so as to cause the sample to adhere to the tip of the probe; and a high voltage generation unit which applies a high voltage to the probe in a state where sample has been collected on the tip of the probe. For example, during measurement, at least one of either the probe or the sample is moved by the displacement unit, causing the tip of the probe to contact or penetrate slightly into the sample, and causing a small quantity of sample to adhere to the probe tip surface. The probe is then moved away from the sample by the displacement unit, and a high voltage is applied to the probe from the high voltage generation unit. Thereupon, a strong electric field acts on the sample adhering to the probe tip, inducing an electrospray phenomenon whereby component molecules in the sample are eliminated and ionized.

Generally, ionization which utilizes the electrospray phenomenon has a higher ionization efficiency when compared to other ionization methods such as ionization methods based on irradiation with laser light. Thus, with a PESI ion source, molecules in a small quantity of sample can be efficiently ionized. Furthermore, it is possible, for example, to perform ionization on a very small quantity of biological tissue collected from a subject in its existing state, without performing any preprocessing, including dissolution or dispersion. Moreover, by changing the location on the sample into which the probe is inserted, ionization can be successively performed on multiple sites in a one-dimensional or two-dimensional region of the sample. This has the advantage of enabling distribution analysis of one-dimensional or two-dimensional regions.

Measurement using a mass analysis device utilizing a PESI ion source (hereinafter referred to as "PESI ionization mass analysis device") is especially promising with respect to measurement of various components in living biological tissue. Namely, as described also in non-patent document 1, for example, a mouse in a living state under anesthesia is placed onto a sample platform in a supine position and laparotomized to expose biological tissue (for example, an organ), into which the probe is directly inserted to collect cells. The cells collected here are in a very small quantity and the insertion of the probe into the biological tissue is also very slight, so injury to the tissue can be kept to a minimum. By utilizing such measurement, it becomes possible to investigate the kinetics of various biochemical reaction cycles, including metabolic pathways, for example, to investigate the kinetics of the TCA (TriCarboxylic Acid) cycle, which is one metabolic pathway, by observing the change over time in acetyl CoA quantity in hepatic tissue after administering bilirubinic acid, which is produced in the glycolysis system, to experimental animals such as mice.

PRIOR ART DOCUMENTS

Patent Documents

Patent document 1: Japanese Unexamined Patent Application Publication 2014-44110

Non-Patent Documents

Non-patent document 1: TAKEDA, Sen and 7 others, "Development of a novel cancer diagnosis assisting device combining mass spectrometry and a statistical learning machine," Shimadzu Hyoron Vol. 69, No. 3•4, March 2013.

SUMMARY OF THE INVENTION

Problem to be Solved by the Invention

However, measurement of biological samples as described above with a conventional PESI ionization mass analysis device entails the following problems.

(1) Under the PESI method, in order to generate charged droplets through application of high voltage, the sample needs to be in a liquid state. Thus, normally, before inserting the probe into biological tissue, a suitable solvent is added dropwise to the biological tissue and a small quantity of cells is collected together with the solvent. Here, blood and the like exuded from the biological tissue mixes with the solvent, forming a sort of contaminant which may make observation of the target component difficult. If the sample is in a living state, there will be substantial exudation of blood and the like from the biological tissue, so the influence of this becomes especially problematic when conducting measurements on a living subject.

(2) In order to observe changes over time in a biochemical reaction such as metabolism, it is necessary to repeatedly perform measurements of the same site of biological tissue of the liver or the like over a certain length of time. However, there are limits to the amount of solvent that can be added dropwise to biological tissue as described above, and the capillary which transports the generated ions from an ambient pressure atmosphere to the mass analysis unit is furthermore heated, so the temperature of the region in which ionization is performed also becomes high under the influence thereof, and the solvent can readily gasify. Thus, sequential measurement over a long period time is difficult.

(3) Blood extracted from biological tissue in a living state coagulates in a relatively short time upon coming into contact with air. Thus, if blood adheres to the surface of the probe, it will gradually coagulate, making it difficult to generate ions derived from the target component by applying high voltage to the probe. As a result, repeated measurement may become difficult.

(4) Biological tissue which is in a living state, even if under anesthesia, moves due to biological reactions and the like. Thus, when one seeks to measure samples collected by repeatedly inserting the probe into the same site of the biological tissue, there is the concern that the probe insertion site will shift and measurement accuracy will be harmed.

It should be noted that even in cases where the measurement object is not a living organism but blood or the like which has just been extracted from a living organism, the problems of (1) and (3) above remain the same.

The present invention was made to resolve the aforementioned problems, its main object being to provide a PESI ionization mass analysis device, and an analysis method for biological samples using said device, which make it possible to repeatedly perform accurate measurements over a relatively long period of time when measuring components in biological tissue of a subject in a living state or components in a sample which has just been extracted from a living organism.

Means for Solving the Problem

The mass analysis device according to the present invention, made to resolve the aforementioned problems, is a mass analysis device which comprises, as an ion source, a conductive probe, a high voltage generation unit which applies a high voltage to said probe, and a displacement unit which causes at least one of either said probe, which is arranged extending in the vertical direction, or a sample arranged below the probe, to move vertically so as to cause the sample to adhere to the tip of said probe, wherein components in the sample are ionized under atmospheric pressure utilizing the electrospray phenomenon, by applying a high voltage to said probe by means of said high voltage generation unit after a portion of the sample has been caused to adhere to the tip of said probe by means of said displacement unit, the mass analysis device being characterized in that it comprises a solvent supply unit which is arranged at a position which is above the sample and through which the tip of said probe passes when at least one of either the probe or the sample is moved by said displacement unit, said solvent supply unit comprising:

a) a container unit which holds solvent inside and which has an aperture in its top surface and bottom surface, through which said probe can be inserted in the direction of its extension, and has a liquid-impervious first membrane member provided so as to occlude the aperture in the bottom surface; and b) a second liquid-impervious membrane member which is provided on the outside of said container unit at a predetermined gap from said first membrane member and whereof the bottom surface contacts the top surface of the sample when the solvent supply unit is arranged over the sample.

Furthermore, the analysis method for biological samples according to the present invention made to resolve the aforementioned problems is an analysis method for biological samples using a mass analysis device according to the present invention as described above, characterized in that, in a state where said solvent supply unit, holding a predetermined solvent in said container unit, has been placed over a biological sample such that the bottom surface of said second membrane member contacts the top surface of the biological sample or the top surface of a measurement target site of the biological sample, by moving at least one of either said probe or said sample by means of said displacement unit, the tip of the probe is made to pass through the solvent in said container unit and is further made to penetrate said first and second membrane members and arrive at said biological sample or said measurement target site, thereby causing a portion of the sample to adhere to the tip of the probe, after which at least one of either said probe or said sample is moved by said displacement unit such that the tip of the probe is moved away from said biological sample or said measurement target site and is made to pass again through the solvent in said container unit and is pulled up to a predetermined position, after which a high voltage is applied to the probe by means of said high voltage generation unit, thereby ionizing the sample collected on the tip of the probe to perform mass analysis.

The term "biological sample" referred to here includes living organisms themselves, solid substances such as biological tissue sections extracted from an organism, bodily fluids such as blood, urine, saliva or gastric juice extracted or derived from an organism, the content of organs such as the stomach, and the like.

The mass analysis device according to the present invention is not particularly limited as to the configuration for performing mass analysis of ions generated in the ion source. Namely, the mass separator which separates ions according to mass-to-charge ratio can be, for example, a quadrupole mass filter, time-of-flight mass separator, ion trap mass separator, Fourier transform ion cyclotron resonance mass separator, etc. Furthermore, it is possible to employ a tandem configuration comprising mass separators before and after a collision cell, or a configuration in which ions are trapped for a time in an ion trap and are dissociated one or multiple times, after which mass analysis is performed in the ion trap itself or in an external mass separator.

However, since the ion source is in a substantially ambient pressure atmosphere and the mass separator is normally kept in a high vacuum atmosphere, a configuration is necessary for transporting ions from ambient pressure to high vacuum, such as a multistage differential pumping system.

In the mass analysis device and analysis method for biological samples using said device according to the present invention, the solvent is held in a container unit, and the tip of the probe for collecting samples passes through this solvent during its relative vertical movement. Thus, solvent adheres to the surface of the probe tip before sample collection, and solvent also adheres to the outer surface of the sample collected on the tip of the probe. As a result, high voltage is applied to the probe in a state where solvent has adequately adhered to the sample, so the electric field acts upon solvent in which components from the sample have dissolved, making it possible to effectively ionize components of the sample. Furthermore, by holding a sufficient quantity of solvent in the container unit, it is possible to avoid drying of the solvent even in the case of measurement performed over a relatively long period of time.

Furthermore, since the tip of the probe pierces the second membrane member when the probe is relatively moved vertically, in the state where the probe has been pulled up, a hole, albeit a small one, remains in the second membrane member. Liquid such as blood from the sample (biological sample) then seeps out through this hole. In the mass analysis device according to the present invention, a predetermined gap is provided between the first membrane member and the second membrane member of the solvent supply unit, so liquid which has seeped out through the hole formed in the second membrane member accumulates in this gap or flows to the outside from this gap. Thus, contamination of the solvent held in the container unit with blood or the like can be kept to a minimum, and reduction in measurement accuracy due to the effects of contaminants contained in the solvent can be prevented. Furthermore, since the solvent itself does not readily mix with blood and since the amount of solvent is large, as described above, the coagulation of blood adhered to the tip of the probe can also be avoided.

It will be noted that water or alcohol is commonly used as the solvent, and it suffices for the first and second membrane members to be able to block these, but since it is desirable for the hole formed through penetration by the probe tip to be small, it is better for the membrane body to have a suitable degree of elasticity. In this connection, the first and second membrane bodies are suitably made from polyvinylidene chloride, polyethylene, polyvinyl chloride, polymethyl pentene or various other single resin materials or composite resin materials combining different resins, of the sort used, for example, in food wrap film.

Furthermore, when the biological sample is the organism itself or a biological tissue section, etc. extracted from the organism, in the analysis method using a mass analysis device according to the present invention, by placing the solvent supply unit over the measurement target site, the measurement target site is lightly pressed down from above. As a result, the measurement target site of the organism cannot move as readily, making it easier for the probe to be inserted into the same location during repeated measurements. In this way, it is possible to improve measurement accuracy in cases where, for example, one wishes to sequentially measure components in cells at the same location over a relatively long period of time.

Furthermore, in the analysis method for biological samples according to the present invention, it is preferable to use a liquid to which an anticoagulant drug has been added as the solvent. As the anticoagulant drug, for example, heparin or the like can be used. This inhibits coagulation in cases where blood becomes mixed into the solvent and makes it possible to more reliably prevent the ionization efficiency from falling due to coagulation of blood on the tip of the probe.

Furthermore, in the mass analysis device according to the present invention, a configuration may be employed which further comprises a sample platform for placing the sample thereon, which allows positional adjustment in the horizontal direction and vertical direction.

Based on this configuration, measurement can be performed at any desired location on the sample by appropriately moving the sample platform with the sample placed thereon in the horizontal plane. Furthermore, by repeatedly performing measurement while moving the sample platform in the horizontal plane, for example, by a predetermined distance each time in orthogonal X axis and Y axis directions, the distribution of a predetermined component and the like can be investigated across a predetermined two-dimensional range of the sample. Furthermore, the insertion depth of the probe into the sample when the probe is lowered can be adjusted by moving the sample platform in the vertical direction according to the size of the sample or the like.

Furthermore, in a device of such configuration, a configuration may be employed which further comprises:

a sample platform drive unit which causes said sample platform to move in the horizontal direction and vertical direction; and a control unit which controls the operation of said sample platform drive unit in response to instructions from outside or in accordance with a predetermined program.

Namely, based on this configuration, presetting the measurement range of a sample, the distance between adjacent measurement locations or the like will allow the control unit to control the operation of the sample platform drive unit, making it possible to automatically carry out measurements across the aforementioned measurement range.

Furthermore, in the mass analysis device according to the present invention, a configuration may be employed in which an arm capable of retaining said solvent supply unit is provided on said sample platform.

Based on this configuration, for example, in cases where the sample platform is moved in order to perform measurement at a different location on the sample, the concern of the solvent supply unit falling from the sample or being shifted out of position is eliminated. Furthermore, the force with which the solvent supply unit presses on the sample from above can be adjusted at one's discretion by means of the arm. Thus, the sample will not be depressed with excessive force, and the stress applied to the sample in cases of measurement over a relatively long period of time can be reduced.

Moreover, this configuration may be made into a configuration further comprising:

an arm drive unit which moves said arm; and a control unit which controls the operation of said arm drive unit in response to instructions from outside or in accordance with a predetermined program.

Based on this configuration, for example, in cases where supply of solvent by the solvent supply unit is not necessary, the solvent supply unit can be withdrawn from above the sample so as not to pose an obstacle to measurement. Furthermore, automatic measurements becomes possible whereby solvent is injected into the container unit of the solvent supply unit at a predetermined location, after which the solvent supply unit is moved over the sample and measurement is then executed, or whereby the solvent supply unit is moved to a predetermined location after completion of measurement and is discarded.

Effect of the Invention

With the mass analysis device and analysis method for biological samples according to the present invention, even in cases of performing measurement of biological samples in a living state, such as biological tissue of experimental animals exposed through laparotomy, it is possible to reduce solvent gasification and the influence of contaminants such as blood, as well as the influence of coagulation of blood and the like, making it possible to sequentially perform high precision measurements over a relatively long period of time.

BRIEF DESCRIPTION OF THE DRAWINGS

FIG. 1 A schematic diagram of a PESI ionization mass analysis device according to an embodiment example of the present invention.

FIG. 2 A simplified longitudinal cross-sectional view of the solvent supply unit in the PESI ionization mass analysis device of the present embodiment example.

FIG. 3 A schematic perspective view of the state of measuring biological tissue of a laparotomized mouse using the PESI ionization mass analysis device of the present embodiment example.

FIG. 4 A schematic perspective view of the sample platform in a PESI ionization mass analysis device according to another embodiment example.

FIG. 5 A schematic drawing illustrating the measurement procedure in the case of toxicological screening performed using the PESI ionization mass analysis device of the present embodiment example.

MODES FOR EMBODYING THE INVENTION

A PESI ionization mass analysis device constituting an embodiment example of the present invention, and an analysis method for biological samples using said device, will be described with reference to the appended drawings. MG. 1 is a schematic diagram of the PESI ionization mass analysis device of the present embodiment example.

The PESI ionization mass analysis device of the present embodiment example has a multistage differential pumping system configuration in which multiple (in this example, two) intermediate vacuum chambers 2 and 3 are provided between an ionization chamber 1 in which ionization of sample components is performed under atmospheric pressure, and an analysis chamber 4 in which mass separation and detection of ions are performed in a high vacuum atmosphere. Although illustration of this has been omitted from FIG. 1, it will be noted that, in general, the inside of the first intermediate vacuum chamber 2 would be evacuated by means of a rotary pump, and the inside of the second intermediate vacuum chamber 3 and analysis chamber 4 would be evacuated by means of a turbomolecular pump in addition to a rotary pump.

A sample platform 7 for placing a sample S onto the top surface thereof is arranged inside an ionization chamber 1, which has a substantially ambient pressure atmosphere, and in the space above the sample platform 7, a metallic probe 6 retained by a probe holder 5 is arranged extending in the vertical direction (Z axis direction). The probe holder 5 with the probe 6 installed thereon is movable in the vertical direction (Z axis direction) by means of a probe drive unit 21 comprising a motor and speed reduction mechanism or actuator, etc. Furthermore, a high voltage on the order of several kV maximum is applied to the probe 6 from a high voltage generation unit 20. The sample platform 7 is movable in three axial directions the two horizontal axis directions (X axis direction and Y axis direction) and the Z axis direction, by means of a sample platform drive unit 23 comprising a motor, speed reduction mechanism, etc. Based on this, the location on the sample S surface contacted by the tip of the probe 6 when the probe 6 is lowered can be moved arbitrarily within the X-Y plane. Furthermore, the sample platform 7 can also be moved in the Z axis direction according to the size of the sample S, making it possible to appropriately adjust the distance between the tip of the probe 6 in its raised position and the top surface of the sample S, and thus the depth of insertion into the sample S when the probe 6 is lowered.

When measurement is to be performed, a solvent supply unit 8, which will be described in detail later, is placed over the sample S. Although not illustrated here, the ionization chamber 1 is provided with a door member, and when this door member is in an opened state, the user can set the sample S or place the solvent supply unit 8 over the sample S.

The inside of the ionization chamber 1 and the inside of the first intermediate vacuum chamber 2 communicate via a desolvation tube 10, which is a small diameter capillary, and due to the pressure difference at the openings at the two ends of the desolvation tube 10, gas from inside the ionization chamber 1 is drawn through the desolvation tube 10 into the first intermediate vacuum chamber 2. Inside the first intermediate vacuum chamber 2, there is arranged an ion guide 11, known as a Q array, in which multiple disc-shaped electrode plates are arranged along ion optical axis C as a single virtual rod electrode, and four virtual rod electrodes are arranged around the ion optical axis C. The inside of the first intermediate vacuum chamber 2 and the inside of the second intermediate vacuum chamber 3 communicate via a small diameter orifice formed at the vertex of a skimmer 12. Inside the second intermediate vacuum chamber 3, an octapole ion guide 13 is installed, in which eight rod electrodes are arranged around the ion optical axis C. Inside the analysis chamber 4 of the final stage, an upstream quadrupole mass filter 14 and downstream quadrupole mass filter 17 are arranged before and after a collision cell 15 there between, each comprising four rod electrodes around the ion optical axis C. Furthermore, inside the collision cell 15, a quadrupole or greater multipole ion guide 16 is arranged, and an ion detector 18 which outputs a signal corresponding to the quantity of arriving ions is arranged after the downstream quadrupole mass filter 17. Illustration of the respective signal lines has been omitted, but a predetermined voltage from voltage generation unit 24 is applied to each component, starting with the desolvation tube 10.

The control unit 25 controls the sample platform drive unit 23, probe drive unit 21, high voltage generation unit 20, voltage generation unit 24, etc. for executing mass analysis of a portion of the sample collected from sample S. Furthermore, detection signals generated by the ion detector 18 are inputted into data processing unit 26, where they are converted to digital data and then subjected to predetermined processing such as generation of a mass spectrum and chromatogram. Furthermore, the control unit 25 has an input unit 27 and display unit 28 connected to it as a user interface.

It will be noted that at least a portion of the functions of the control unit 25 and data processing unit 26 can generally be implemented using a personal computer as a hardware resource, by causing specialized control and processing software which has been preinstalled on said person computer to run on the computer.

FIG. 2 is a schematic longitudinal cross-sectional view of the vicinity of the solvent supply unit 8 shown in FIG. 1, and FIG. 3 is a schematic perspective view of a situation where a portion of the cells from the biological tissue of a living mouse is to be collected and analyzed by means of the PESI ionization mass analysis device of the present embodiment example.

First, the configuration of the solvent supply unit 8 will be described in detail.

The solvent supply unit 8 comprises a cylindrical member 80 made of synthetic resin with an open top surface and bottom surface, an upper membrane member 81 made of polyvinylidene chloride stretched liquid-tight so as to occlude the aperture in the bottom surface of the cylindrical member 80, and a lower membrane member 82 made of polyvinylidene chloride, stretched below the upper membrane member 81 and substantially parallel to said membrane member 81 so as to sandwich a spacer 83. The upper membrane member 81 corresponds to the first membrane member of the present invention, and the lower membrane member 82 corresponds to the second membrane member of the present invention. Furthermore, the cylindrical member 80 and the upper membrane member 81 stretched over its bottom surface, as shown in FIG. 2 and FIG. 3, constitute a container capable of holding solvent 84 on the inside, corresponding to the container unit of the present invention. Here, a cylindrical member 80 with a fully opened top surface and bottom surface is used as a constituent element of the container unit, but it is also possible for the top surface and bottom surface to be closed, with only a portion open.

The gap between the upper membrane member 81 and the lower membrane member 82 is the thickness d of the spacer 83. The spacer 83 is, for example, suitably made in a substantially flat cylindrical shape and is provided with an aperture through which liquid can pass at a suitable location on its wall surface. The upper membrane member 81 and lower membrane member 82 both have liquid impermeability, and preferably have a suitable degree of elasticity. Thus, in the present embodiment example, polyvinylidene chloride was used for the upper membrane member 81 and lower membrane member 82, but the material is not limited thereto, and other single resin materials or composite resins combining different materials, such as polyethylene, polyvinyl chloride, polymethyl pentene and the like can also be used.

As an example, the inside diameter of the cylindrical member 80 is 9.4 [mm] and the height is 5.0 [mm]. Furthermore, the membrane thickness of the upper membrane member 81 and lower membrane member 82 is 11 [μm]. Furthermore, the distance d between the upper membrane member 81 and lower membrane member 82 is 1.0 [mm]. Furthermore, the solvent 84 is generally water, alcohol or a mixture thereof. In this example, a solvent made by adding the anticoagulant drug heparin (0.5 [mg/mL]) for preventing coagulation of blood to 100 [μL] of 50% ethanol aqueous solution was used. The cylindrical member 80 can of course be modified to any shape so long as it, together with the upper membrane member 81, can constitute a container unit capable of holding solvent.

Next, the procedure and operation will be described for the case where real time analysis is performed on components in the liver cells of a live mouse using the PESI ionization mass analysis device of the present embodiment example.

As shown in FIG. 3, the user laparotomizes an anesthetized mouse 100 and places it in a supine position on the sample platform 7. The solvent supply unit 8 holding solvent 84 is then placed over the upward facing exposed measurement target site, i.e. the liver 101. When the solvent supply unit 8 has been placed in this manner, the bottom surface of the lower membrane member 82 sits tights against the liver 101 of the mouse 100. Here, the solvent supply unit 8 may also be secured to the liver 101 using a small amount of adhesive. It will be noted that the solvent 84 is preferably put in, as much as possible, right before performing analysis, so it is better to inject the solvent right before analysis, after first placing the empty solvent supply unit 8 over the liver 101.

After the preparation described above has been completed, the user instructs the initiation of analysis via the input unit 27, whereupon the control unit 25, having received this instruction, sends control signals to the various units for performing analysis. It will be noted that the ionization chamber 1, as described above, is provided with a door member for taking out and putting in samples, and normally, analysis cannot be initiated unless the door member has been fully closed, but when analyzing a large sample such as the experimental animal itself, it may be difficult to fully close the door member in some cases. Thus, in the device of the present embodiment example, by performing a predetermined manipulation with the input unit 27, it is possible to initiate analysis even in cases where the door member of the ionization chamber 1 has not been closed, that is, in cases where the switch which senses closure of the door member does not turn on.

Once analysis has been initiated, the probe drive unit 21, under the control of the control unit 25, is lowered to a position (for example, the position of dotted line 6' in FIG. 2) at which the tip thereof is slightly inserted into the liver 101 (sample S), after which the probe 6 is raised to a predetermined position. When the probe 6 is lowered, the sharp tip of the probe 6 passes through the solvent 84 held in the solvent supply unit 8 and further pierces the upper membrane member 81 and lower membrane member 82 to reach the sample S. Therefore, solvent adheres to the outside surface of the tip of the probe 6, wetting it with solvent. When the tip of the probe is then inserted into the liver 101, a portion of the cells of the liver 101 adheres to the tip of the probe 6. When the probe 6 is pulled up, the tip of the probe 6 again passes through the solvent 84, so solvent adheres also to the outer surface of the liver cells adhering to the tip of the probe 6. As a result, the liver cells adhering to the tip of the probe 6 come to be encased in solvent, and the components in the cells dissolve in the solvent and turn into a liquid sample.

After the probe 6 has been pulled up to a predetermined position, the high voltage generation unit 20 applies a predetermined high voltage to the probe 6. It will be noted that the polarity of the high voltage applied to the probe 6 depends on the polarity of the ions which are the object of measurement. When a high voltage is applied to the tip of the probe 6, a large electric field acts upon the liquified sample adhering to the tip of the probe 6, and components in the sample are dissociated with a biased charge (i.e., are electrosprayed) due to Coulombic repulsion, etc. In this process, the components are ionized. The ions generated as a result are sucked into the desolvation tube 10 with the gas flow generated by the pressure differential described above, and are fed into the first intermediate vacuum chamber 2.

Since the upper membrane member 81 and lower membrane member 82 both possess a suitable degree of elasticity, as described above, the holes formed through penetration by the tip of the probe 6 shrink to a certain extent when the probe 6 is pulled up. However, since these holes are not fully occluded, liquid such as blood which seeps out from the liver 101 due to the insertion of the probe 6 will leak out onto the lower membrane member 82 through the small hole. There is a space with a suitable gap between the upper membrane member 81 and lower membrane member 82, and liquid does not leak out in a sufficiently large quantity to fill this space in a short time. Thus, blood or other liquid which leaks out into this space spreads toward the periphery of the top of the lower membrane member 82, and is discharged to the outside of the spacer 83 through the aperture formed in the spacer 83. The blood or other liquid which seeps out from the liver 101 can thereby be prevented from being mixed into the solvent 84 inside the container unit of the solvent supply unit 8. Of course, the blood or other liquid adhering to the liver cells when the probe 6 is pulled out will be mixed into the solvent 84 inside the container unit, but the quantity thereof is extremely small and not enough to hinder observation.

Ions derived from the sample which have been fed into the first intermediate vacuum chamber 2 as described above are transported while being converged by the high frequency electric field formed by ion guide 11, and fed into the second intermediate vacuum chamber 3 through the orifice at the vertex of the skimmer 12. Moreover, the ions are fed to the analysis chamber 4 while being converged by the high frequency electric field formed by ion guide 13. A voltage obtained by superimposing high frequency voltage onto the direct current voltage from the high voltage generation unit 24 is applied to the upstream quadrupole mass filter 14, and in response to this voltage, only ions having the mass-to-charge ratio m/z corresponding to that voltage pass through the space in the long axis direction of the upstream quadrupole mass filter 14 and enter the collision cell 15. Argon gas or the like is introduced as collision gas into the collision cell 15, and upon entering the collision cell 15, the ions come into contact with said gas and dissociate. The product ions generated through this dissociation are converted by the high frequency electric field formed by ion guide 16, exit the collision cell 15 and are introduced into the downstream quadrupole mass filter 17. A voltage obtained by superimposing high frequency voltage onto the direct current voltage from the high voltage generation unit 24 is applied also to the downstream quadrupole mass filter 17, and only product ions having a mass-to-charge ratio m/z corresponding to that voltage pass through the space in the long axis direction of the downstream quadrupole mass filter 17 and reach the ion detector 18.

For example, in order to allow only ions having a specified mass-to-charge ratio to pass through the upstream quadrupole mass filter 14 and perform mass scanning across a predetermined mass-to-charge ratio range at the downstream quadrupole mass filter 17, a product ion spectrum which reflects various product ions obtained by dissociating ions having a specified mass-to-charge ratio derived from the sample can obtained in the data processing unit 26. Of course, besides product ion scan measurements, precursor ion scan measurements, neutral loss scan measurements and MRM measurements may also be carried out, and SIM measurements and regular scan measurements without dissociation of ions in the collision cell 15 may be performed as well.

For example, if one wishes to observe the change over time in the quantity of acetyl CoA in the liver after administering bilirubinic acid to mice, the measurement as described above would be repeated at predetermined time intervals. A large quantity of solvent 84 is provided in the solvent supply unit 8, so even if a certain degree of gasification should occur during measurement, the solvent 84 will not dry up and sequential measurement over a long period of time is possible. Furthermore, the solvent supply unit 8 functions as a type of weight, so movement of the living liver 101 is constrained and the tip of the probe 6 can be repeatedly inserted into substantially the same location of the liver 101. It is thereby possible to reduce shifting of the measurement location during repeated measurement, making it possible to accurately ascertain change over time of the target component.

In the case where one wishes to investigate the distribution of the target compound over a predetermined two-dimensional range of the liver 101, the measurement parameters, such as the range and the step width of movement in the X axis and Y axis directions, are set via the input unit 27. The control unit 25 controls the sample platform drive unit 23 according to these measurement parameters, moving the probe 6 up and down and moving the sample platform 7 by a predetermined step width in the X axis or Y axis direction for each measurement or for a certain number of measurement. This can be repeated to perform measurements on multiple measurement points within a predetermined two-dimensional range.

FIG. 4 is a schematic perspective view of the sample platform in a PESI ionization mass analysis device according to another embodiment example of the present invention.

In the embodiment example described above, the solvent supply unit 8 was placed over the measurement target site, while in the mass analysis device of this embodiment example, an arm 30, which is rotatable about a vertical axis and vertically displaceable, is provided on the sample platform 7 as a retaining member which retains the solvent supply unit 8. The arm 30 comprises a grip 31 at its end for gripping the cylindrical member 80. The arm 30 is rotationally and vertically driven by an arm drive unit 32 comprising a motor, etc. By means of this, it is possible, for example, to operate the arm 30 so as to lightly press the solvent supply unit 8 against the top of the sample measurement site (the position indicated by reference symbol 8' in FIG. 4). Furthermore, prior to performing measurement, the solvent supply unit 8 can be moved to a predetermined solvent injection location to automatically or manually inject the solvent. Furthermore, after completion of measurement, the solvent supply unit 8 can be moved to a predetermined discarding location to drop the solvent supply unit 8, making it possible to discard used solvent supply units 8.

The PESI ionization mass analysis device of the present embodiment example illustrated in FIG. 1 is not only for directly measuring components in biological tissue of mice or other experimental animals in a living state as described above, but is also useful for measurement of components in various types of samples extracted from biological organisms. FIG. 5 is a schematic drawing illustrating the measurement procedure in the case of toxicological screening performed using the PESI ionization mass analysis device of the embodiment example described above.

As shown in FIG. 5 ($a$), the top surface of the sample plate 200 used for measurement has a concave part 201 capable of holding a small quantity of liquid formed in it. The liquid sample 202, such as a small quantity of blood (or other dilution) collected from a human or other subject, is added dropwise to the concave part 201 until it bulges up due to surface tension (see FIG. 5 ($b$)). The sample plate 200 is then set at a predetermined position inside the ionization chamber 1, and the solvent supply unit 8, holding a solvent such as heparin-containing ethanol aqueous solution, is installed over the liquid sample 202 in the recessed part 201, as shown in FIG. 5 ($c$). Here, the bottom surface of the lower membrane member 82 sits tightly against the top surface of the liquid sample 202. Subsequently, as shown in FIG. 5 ($d$), the probe 6 is lowered and its tip is immersed in the liquid sample 202, the probe 6 is then pulled up to a predetermined position and measurement is performed to detect compounds contained in the liquid sample 202.

The inventors performed an experiment to confirm that compounds known to be toxicants can be suitably detected by the procedure described above. For the experiment, multiple samples were prepared, consisting of blood serum with standard solutions of twelve drug substances, including narcotics, psychotropic agents and dangerous drugs (amphetamine, methamphetamine, cocaine, diazepam, paroxetine, fluvoxamine, chlorpromazine, zolpidem, acetyl fentanyl, diphenidine, JWH-018 and α-PHP) added thereto at a suitable concentration in the range of 0.1 to 100 [ng/mL]. 20

[μL] of these serum samples was collected and added dropwise to the recessed part 201 on the sample plate 200 without performing any preprocessing, after which a solvent supply unit 8 filled with 30 [μL] of 50% ethanol aqueous solution containing heparin at a concentration of 1 [mg/mL] was placed over the serum sample. Mass analysis was then performed in MRM measurement mode based on MRM transitions corresponding to each of the aforementioned twelve drug substances. The time required for measurement was 0.3 minutes, and detection result for each drug substance was outputted after completion of measurement essentially without delay.

The result of the above experiment confirmed that all of the aforementioned twelve drug substances could be detected directly from serum samples. The lower limit of detection of the drug substances in MRM measurement mode was about 10 [ng/mL] for amphetamine, methamphetamine, cocaine, paroxetine, fluvoxamine, chlorpromazine, diphenidine and JWH-018 and about 1 [ng/mL] for diazepam, acetyl fentanyl and α-PHP, while zolpidem was detectable even at about 0.1 [ng/mL]. Based on this, it can be concluded that the above-described measurement method allows low drug substance concentrations on the order of 10 [ng/mL] to be detected directly from a subject's blood.

Furthermore, to study the quantitative characteristics of the present measurement method, the quantitative characteristics for diazepam were verified using diazepam-5d as an internal standard, whereupon the calibration curve showed good linearity, with $R^2$ being 0.99. It was thus confirmed that, at least for diazepam, not only detection of the compound but also adequate quantitation is possible.

Generally, in testing for drug substances in blood as above, component separation preprocessing through LC, GC, etc. is necessary, so in actuality, it takes 2 to 3 for the results to be produced. By contrast, with the measurement method described above, sample preprocessing operations are unnecessary, and detection results can generally be obtained within one minute.

This method is therefore very useful for toxicological screening tests and the like, where rapidity is especially required. The samples to be tested are of course not limited to blood and can also be urine, etc.

Furthermore, in addition to toxicological screening tests, the measurement method described above can be applied in various fields where rapid analysis is required. For example, in critical care and emergency medicine, by rapidly detecting compounds contained in a subject's vomit and excreta or in the liquid discharged during gastric lavage or the like, it becomes possible to rapidly perform the appropriate measures and treatment, increasing the likelihood of life-saving and allowing unnecessary procedures which would be a burden on the subject to be eliminated.

It will be noted that the embodiment example described above is just one example of the present invention, and suitable modifications, alterations and additions made within the scope of the gist of the present invention are of course also included within the scope of patent claims of the present application.

For example, the PESI ionization mass analysis device in the embodiment example described above had a tandem quadrupole configuration, but as discussed above, the configuration of the mass separator, etc. is of course not limited to this.

EXPLANATION OF REFERENCES

1 . . . Ionization chamber
2 . . . First intermediate vacuum chamber
3 . . . Second intermediate vacuum chamber
4 . . . Analysis chamber
5 . . . Probe holder
6 . . . Probe
7 . . . Sample platform
8 . . . Solvent supply unit
80 . . . Cylindrical member
81 . . . Upper membrane member
82 . . . Lower membrane member
83 . . . Spacer
84 . . . Solvent
10 . . . Desolvation tube
11, 13, 16 . . . Ion guide
12 . . . Skimmer
14 . . . Upstream quadrupole mass filter
15 . . . Collision cell
17 . . . Downstream quadrupole mass filter
18 . . . Ion detector
20 . . . High voltage generation unit
21 . . . Probe drive unit
23 . . . Sample platform drive unit
24 . . . Voltage generation unit
25 . . . Control unit
26 . . . Data processing unit
27 . . . Input unit
28 . . . Display unit
30 . . . Arm
31 . . . Grip
32 . . . Arm drive unit
100 . . . Mouse
101 . . . Liver
200 . . . Sample plate
201 . . . Recessed part
202 . . . Liquid sample
C . . . Ion optical axis
S . . . Sample

The invention claimed is:

1. A mass analysis device which comprises, as an ion source, a conductive probe, a high voltage generation unit which applies a high voltage to said probe, and a displacement unit which causes at least one of either said probe, which is arranged extending in the vertical direction, or a sample arranged below the probe, to move vertically so as to cause the sample to adhere to the tip of said probe, wherein components in the sample are ionized under atmospheric pressure utilizing the electrospray phenomenon, by applying a high voltage to said probe by means of said high voltage generation unit after a portion of the sample has been caused to adhere to the tip of said probe by means of said displacement unit, the mass analysis device being characterized in that it comprises a solvent supply unit which is arranged at a position which is above the sample and through which the tip of said probe passes when at least one of either the probe or the sample is moved by said displacement unit, said solvent supply unit comprising:

a) a container unit which holds solvent inside and which has an aperture in its top surface and bottom surface, through which said probe can be inserted in the direction of its extension, and has a liquid-impervious first membrane member provided so as to occlude the aperture in the bottom surface; and b) a second liquid-impervious membrane member which is provided on the outside of said container unit at a predetermined gap from said first membrane member and whereof the bottom surface contacts the top surface of the sample when the solvent supply unit is arranged over the sample.

2. A mass analysis device as set forth in claim 1, characterized in that it further comprises a sample platform for placing the sample thereon, which allows positional adjustment in the horizontal direction and vertical direction.

3. A mass analysis device as set forth in claim 2, characterized in that it further comprises:
   a sample platform drive unit which causes said sample platform to move in the horizontal direction and vertical direction; and
   a control unit which controls the operation of said sample platform drive unit in response to instructions from outside or in accordance with a predetermined program.

4. A mass analysis device as set forth in claim 2, characterized in that an arm capable of retaining said solvent supply unit is provided on said sample platform.

5. A mass analysis device as set forth in claim 4, characterized in that it further comprises:
   an arm drive unit which moves said arm; and
   a control unit which controls the operation of said arm drive unit in response to instructions from outside or in accordance with a predetermined program.

6. An analysis method for biological samples using a mass analysis device as set forth in claim 1, characterized in that,
   in a state where said solvent supply unit, holding a predetermined solvent in said container unit, has been placed over a biological sample such that the bottom surface of said second membrane member contacts the top surface of the biological sample or the top surface of a measurement target site of the biological sample,
   by moving at least one of either said probe or said sample by means of said displacement unit, the tip of the probe is made to pass through the solvent in said container unit and is further made to penetrate said first and second membrane members and arrive at said biological sample or said measurement target site, thereby causing a portion of the sample to adhere to the tip of the probe, after which
   at least one of either said probe or said sample is moved by said displacement unit such that the tip of the probe is moved away from said biological sample or said measurement target site and is made to pass again through the solvent in said container unit and is pulled up to a predetermined position, after which a high voltage is applied to the probe by means of said high voltage generation unit, thereby ionizing the sample collected on the tip of the probe to perform mass analysis.

7. A method of analysis for biological samples as set forth in claim 6, characterized in that a liquid to which an anticoagulant drug has been added is used as said solvent.

8. An analysis method for biological samples using a mass analysis device as set forth in claim 2, characterized in that,
   in a state where said solvent supply unit, holding a predetermined solvent in said container unit, has been placed over a biological sample such that the bottom surface of said second membrane member contacts the top surface of the biological sample or the top surface of a measurement target site of the biological sample,
   by moving at least one of either said probe or said sample by means of said displacement unit, the tip of the probe is made to pass through the solvent in said container unit and is further made to penetrate said first and second membrane members and arrive at said biological sample or said measurement target site, thereby causing a portion of the sample to adhere to the tip of the probe, after which
   at least one of either said probe or said sample is moved by said displacement unit such that the tip of the probe is moved away from said biological sample or said measurement target site and is made to pass again through the solvent in said container unit and is pulled up to a predetermined position, after which a high voltage is applied to the probe by means of said high voltage generation unit, thereby ionizing the sample collected on the tip of the probe to perform mass analysis.

9. An analysis method for biological samples using a mass analysis device as set forth in claim 3, characterized in that,
   in a state where said solvent supply unit, holding a predetermined solvent in said container unit, has been placed over a biological sample such that the bottom surface of said second membrane member contacts the top surface of the biological sample or the top surface of a measurement target site of the biological sample,
   by moving at least one of either said probe or said sample by means of said displacement unit, the tip of the probe is made to pass through the solvent in said container unit and is further made to penetrate said first and second membrane members and arrive at said biological sample or said measurement target site, thereby causing a portion of the sample to adhere to the tip of the probe, after which
   at least one of either said probe or said sample is moved by said displacement unit such that the tip of the probe is moved away from said biological sample or said measurement target site and is made to pass again through the solvent in said container unit and is pulled up to a predetermined position, after which a high voltage is applied to the probe by means of said high voltage generation unit, thereby ionizing the sample collected on the tip of the probe to perform mass analysis.

10. An analysis method for biological samples using a mass analysis device as set forth in claim 4, characterized in that,
   in a state where said solvent supply unit, holding a predetermined solvent in said container unit, has been placed over a biological sample such that the bottom surface of said second membrane member contacts the top surface of the biological sample or the top surface of a measurement target site of the biological sample,
   by moving at least one of either said probe or said sample by means of said displacement unit, the tip of the probe is made to pass through the solvent in said container unit and is further made to penetrate said first and second membrane members and arrive at said biological sample or said measurement target site, thereby causing a portion of the sample to adhere to the tip of the probe, after which
   at least one of either said probe or said sample is moved by said displacement unit such that the tip of the probe is moved away from said biological sample or said measurement target site and is made to pass again through the solvent in said container unit and is pulled up to a predetermined position, after which a high voltage is applied to the probe by means of said high voltage generation unit, thereby ionizing the sample collected on the tip of the probe to perform mass analysis.

11. An analysis method for biological samples using a mass analysis device as set forth in claim 5, characterized in that, in a state where said solvent supply unit, holding a predetermined solvent in said container unit, has been placed over a biological sample such that the bottom surface of said second membrane member contacts the top surface of the biological sample or the top surface of a measurement target site of the biological sample, by moving at least one of either said probe or said sample by means of said displacement unit, the tip of the probe is made to pass through the solvent in said container unit and is further made to penetrate said first and second membrane members and arrive at said biological sample or said measurement target site, thereby causing a portion of the sample to adhere to the tip of the probe, after which at least one of either said probe or said sample is moved by said displacement unit such that the tip of the probe is moved away from said biological sample or said measurement target site and is made to pass again through the solvent in said container unit and is pulled up to a predetermined position, after which a high voltage is applied to the probe by means of said high voltage generation unit, thereby ionizing the sample collected on the tip of the probe to perform mass analysis.

* * * * *